United States Patent
Zhao et al.

(10) Patent No.: US 10,123,690 B2
(45) Date of Patent: Nov. 13, 2018

(54) SYSTEM AND METHOD FOR MEASURING DYSPHOTOPSIA

(71) Applicant: ABBOTT MEDICAL OPTICS INC., Santa Ana, CA (US)

(72) Inventors: Huawei Zhao, Irvine, CA (US); Mihai State, Groningen (NL); Luuk Franssen, Groningen (NL); Patricia Ann Piers, Groningen (NL); Hendrik A. Weeber, Groningen (NL); Marrie Van Der Mooren, Engelbert (NL)

(73) Assignee: JOHNSON & JOHNSON SURGICAL VISION, INC., Santa Ana, CA (US)

( * ) Notice: Subject to any disclaimer, the term of this patent is extended or adjusted under 35 U.S.C. 154(b) by 0 days.

(21) Appl. No.: 15/417,136

(22) Filed: Jan. 26, 2017

(65) Prior Publication Data
US 2017/0135570 A1    May 18, 2017

Related U.S. Application Data

(62) Division of application No. 14/554,564, filed on Nov. 26, 2014, now Pat. No. 9,554,696.
(Continued)

(51) Int. Cl.
*A61B 3/00* (2006.01)
*G01M 11/02* (2006.01)
(Continued)

(52) U.S. Cl.
CPC .............. *A61B 3/0025* (2013.01); *A61B 3/10* (2013.01); *G01M 11/0207* (2013.01); *A61F 2/16* (2013.01)

(58) Field of Classification Search
None
See application file for complete search history.

(56) References Cited

U.S. PATENT DOCUMENTS

| 4,437,733 A | 3/1984 | Takahashi et al. |
| 5,042,938 A | 8/1991 | Shimozono |

(Continued)

FOREIGN PATENT DOCUMENTS

| EP | 2631891 A1 | 8/2013 |
| WO | 0185016 A2 | 11/2001 |

(Continued)

OTHER PUBLICATIONS

International Search Report and Written Opinion for Application No. PCT/US07/75623, dated Aug. 11, 2008, 6 pages.
(Continued)

*Primary Examiner* — Shawn Decenzo
(74) *Attorney, Agent, or Firm* — Johnson & Johnson Surgical Vision, Inc.

(57) ABSTRACT

Systems and methods for measuring dysphotopsia are provided. These systems and methods can be used to objectively quantify positive and negative dysphotopsia. One embodiment provides a system and method for determining dysphotopsia that uses a first light source configured to provide light energy to illuminate a model eye, a refractor for refracting the light energy from the first light source and directing it into the model eye, a first electronic light sensor for measuring an amount of light in the model eye; a second light source configured to provide light energy to illuminate the model eye, wherein the light energy from the second light source is introduced at an angle from the first light source; and a second electronic light sensor for measuring the amount of light in the model eye, wherein the second electronic light sensor is capable of taking measurements from various points around the model eye. Data from these
(Continued)

measurements can then analyzed to provide an objective measurement of dysphotopsia.

18 Claims, 8 Drawing Sheets

Related U.S. Application Data

(60) Provisional application No. 61/909,210, filed on Nov. 26, 2013.

(51) Int. Cl.
*A61B 3/10* (2006.01)
*A61F 2/16* (2006.01)

(56) References Cited

U.S. PATENT DOCUMENTS

| | | | |
|---|---|---|---|
| 5,379,110 | A | 1/1995 | Matsui et al. |
| 6,241,356 | B1 | 6/2001 | Von Wallfeld et al. |
| 6,550,917 | B1 | 4/2003 | Neal et al. |
| 6,786,603 | B2 | 9/2004 | Altmann |
| 6,817,714 | B2 | 11/2004 | Altmann |
| 7,281,797 | B2 | 10/2007 | Yamaguchi et al. |
| 7,296,893 | B2 | 11/2007 | Dai |
| 7,339,539 | B2 | 3/2008 | Joannopoulos et al. |
| 7,547,102 | B2 | 6/2009 | Dai |
| 7,726,813 | B2 | 6/2010 | Dai |
| 7,784,946 | B2 * | 8/2010 | LeBlanc ............ A61B 3/132 351/210 |
| 7,911,211 | B2 | 3/2011 | Crain et al. |
| 7,931,374 | B2 * | 4/2011 | Dai .................. A61B 3/1015 351/205 |
| 8,123,357 | B2 | 2/2012 | Dai et al. |
| 9,211,061 | B2 | 12/2015 | Kasthurirangan et al. |
| 2003/0163122 | A1 | 8/2003 | Sumiya |
| 2003/0189690 | A1 | 10/2003 | Mihashi et al. |
| 2004/0057010 | A1 | 3/2004 | Altmann |
| 2004/0260275 | A1 | 12/2004 | Liang et al. |
| 2005/0195364 | A1 | 9/2005 | Dai |
| 2006/0274268 | A1 | 12/2006 | Andino et al. |
| 2007/0195265 | A1 | 8/2007 | Dreher et al. |
| 2007/0211214 | A1 | 9/2007 | Dai |
| 2007/0285617 | A1 | 12/2007 | Mills et al. |
| 2008/0198331 | A1 | 8/2008 | Azar et al. |
| 2009/0168019 | A1 | 7/2009 | Tuan |
| 2009/0231546 | A1 | 9/2009 | Dai |
| 2010/0179793 | A1 | 7/2010 | Chernyak et al. |
| 2010/0234833 | A1 | 9/2010 | Dai |
| 2011/0149236 | A1 | 6/2011 | Weeber |

FOREIGN PATENT DOCUMENTS

| | | |
|---|---|---|
| WO | 04028356 A1 | 4/2004 |
| WO | 2004053568 A1 | 6/2004 |
| WO | 2012074742 A1 | 6/2012 |

OTHER PUBLICATIONS

International Search Report and Written Opinion for Application No. PCT/US2014/067642, dated Feb. 10, 2015, 7 pages.

Klein S.A., "Optimal Corneal Ablation for Eyes with Arbitrary Hartmann-Shack Aberrations," Journal of the Optical Society of America A, 1998, vol. 15 (9), pp. 2580-2588.

Liang J., et al, "Objective Measurement of Wave Aberrations of the Human Eye With the Use of a Hartmann-Shack Wave-Front Sensor," Journal of the Optical Society of America, 1994, vol. 11 (7), pp. 1949-1957.

Supplementary European Search Report for Application No. EP05723677 dated Feb. 3, 2010, 4 pages.

Supplementary European Search Report for Application No. EP07840839, dated Nov. 28, 2013, 11 pages.

\* cited by examiner

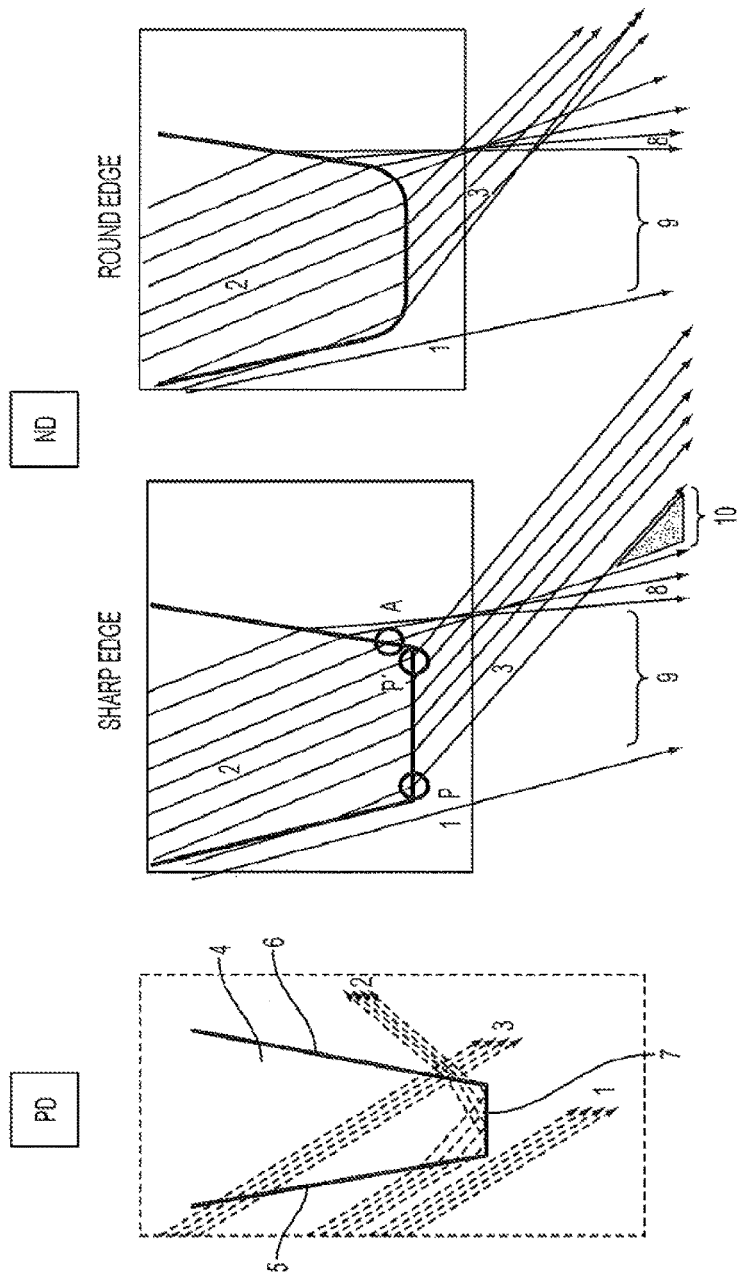

SYSTEM AND METHOD FOR MEASURING DYSPHOTOPSIA

CROSS-REFERENCES TO RELATED APPLICATIONS

This application claims priority to and is a divisional of U.S. patent application Ser. No. 14/554,564, filed Nov. 26, 2014, which claims priority to U.S. Provisional Application No. 61/909,210 filed on Nov. 26, 2013, the entire contents of which are incorporated herein by reference.

TECHNICAL FIELD

This invention relates to vision techniques and particularly to techniques for measuring dysphotopsia.

BACKGROUND OF THE INVENTION

Intraocular lenses (IOL) are typically implanted during cataract surgery where the natural lens is replaced with an IOL. Currently the majority of commercially available IOLs are either circular shaped or plate shaped with an embedded circular optic body in the middle of the plate. Both shapes result in clinically observed light artifacts, generically called dysphotopsia, which may be bothersome to the person with the implanted IOL.

There are two types of dysphotopsia: positive dysphotopsia (PD) and negative dysphotopsia (ND). PD defines unexpected "bright" images such as arcs or rings while ND refers to unexpected "dark" images such as shadows or lines. While PD is determined by light reflected by the edge of the IOL, ND arises from both light refracted by the edge of the IOL as well as light that passes through the eye without encountering the IOL.

Due to the bothersome nature of PD and ND, it would be beneficial if the amount of PD and ND resulting from a particular IOL design could be measured. IOL design modifications could then be made in order to reduce or eliminate PD and/or ND. Currently, in either laboratory or clinic environments, there are no metrics for the objective measurement of PD or ND.

For these and other reasons there is a continuous need for the development of improved devices and techniques aiming to qualitatively and quantitatively measure PD and ND.

BRIEF SUMMARY OF THE INVENTION

Embodiments of the present invention generally provide systems and methods for measuring PD and/or ND. These systems and methods can be used to quantify PD and/or ND and include the following: a first light source configured to provide light energy to illuminate a model eye; a refractor for refracting the light energy from the first light source and directing it into the model eye; a first electronic light sensor for measuring an amount of light in the model eye; a second light source configured to provide light energy to illuminate the model eye, wherein the light energy from the second light source is introduced at an angle from the first light source; and a second electronic light sensor for measuring the amount of light in the model eye, wherein the second electronic light sensor is capable of taking measurements from various points around the model eye. The system may further include a focusing lens, an aperture and a beam splitter, wherein the light energy provided by the first light source travels through the focusing lens, aperture, and beam splitter prior to travelling through the refractor. The aperture may have a filter for varying the wavelength and/or light intensity. The refractor may have a plurality of focusing lenses and a plurality of mirrors. The model eye may have a population average cornea simulating lens (ACE) or may be an eye model that does not have a cornea. The model eye may have a pupil that is an aperture or a slit. The aperture may be circular or poly-angular. The electronic light sensors are selected from the group consisting of: CCD cameras, CMOS detectors, wavefront sensors, and interferometers. The system may further comprise a guide along which the second electronic light sensor travels in order to take measurements from various points around the model eye. In another embodiment, rather than have one second electronic light sensor take measurements at various points around the eye, a plurality of electronic light sensors may be located at various points around the eye. It is further envisioned that the plurality of electronic light sensors may be part of an integrating sphere.

In another embodiment, a method for measuring dysphotopsia is envisioned, wherein the method comprises: illuminating a model eye with a first light source; measuring the light energy introduced by the first light source with a first electronic light sensor stationed behind the model eye and generating first data; measuring the light energy introduced by the first light source with a second electronic light sensor and generating second data, wherein the second light sensor measures the light energy from multiple points around the model eye; illuminating the model eye with a second light source, wherein the second light source introduces light at an angle from the first light source; measuring the light energy introduced by the second light source with the first electronic light sensor and the second electronic light sensor to generate third and fourth data respectively; and analyzing the first data, second data, third data, and fourth data to determine a measurement for dysphotopsia. The light energy introduced by the first and second light source may be measured along the radial direction by the second electronic light sensor. The light energy introduced by the first and second light source may also be measured along the angular direction by the second electronic light sensor.

In another embodiment, the dysphotopsia measurement system and/or method comprises an object generator placed on a pivot arm (0-90°) and containing a light source, a plurality of filters (discrete wavelengths, photopic) and targets (slits, circular etc.); a wide angle physical eye model constructed with or without a (ACE) cornea, a circular pupil, an IOL holder with the IOL and a back window (flat or curved); a flat electronic light sensor (CCD camera or other) placed on a X and/or Y, Z translation stage that enables the capture of the eye model refracted light for various pivot arm angular positions thus detecting spurious images associated with both PD and ND.

In another embodiment, a method for measuring dysphotopsia comprises theoretically calculating the image heights and/or defocusing values for the main image and ND and PD for a given object angle and using the image heights and/or defocusing values as inputs for the in-vitro measurements. A method for measuring dysphotopsia may also comprise acquiring the frames corresponding to the main image and the photic events for a given object angle, and then processing them in-line or off-line to compute the average per frame intensity profiles normalized by the shutter time. One may then perform the pixel-to-mm conversion to determine the image height values for the main image and the photic events.

The above summary and the following detailed description are merely exemplary, illustrative, and explanatory, and are not intended to limit, but to provide further explanation of the invention as claimed. Additional features and advantages of the invention will be set forth in the ensuing detailed descriptions that follow, and in part, will be apparent from the description, or may be learned by practicing various embodiments of the invention. The objectives and other advantages of the invention will be realized by the structures and methods particularly pointed out in the written description and claims as well as the accompanying drawings.

BRIEF DESCRIPTION OF THE DRAWINGS

FIG. 1 is a side view of an intraocular lens;
FIG. 2 is a side view of an intraocular lens;
FIG. 3 is a side view of an intraocular lens.

DETAILED DESCRIPTION OF THE INVENTION

Figure 4:
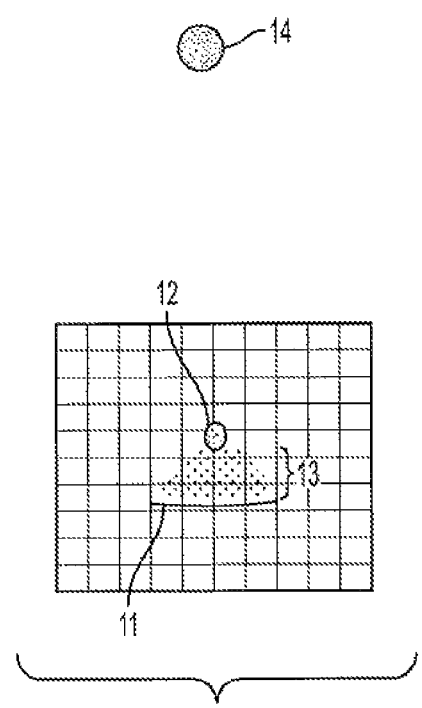
FIG. 4 is a diagram illustrating negative dysphotopsia.

The figures and descriptions of the present invention have been simplified to illustrate elements that are relevant for a clear understanding of the present invention, while eliminating, for the purpose of clarity and brevity, many other elements found in typical ophthalmic techniques, systems, methods, lenses, and implantable optic apparatuses. Those of ordinary skill in the art may thus recognize that other elements and/or steps are desirable and/or required in implementing the present invention. However, because such elements and steps are well known in the art, and because they do not necessarily facilitate a better understanding of the present invention, those elements and steps are not discussed. This disclosure is directed to all applicable variations, changes, and modifications known to those skilled in the art. As such, the following detailed descriptions are merely illustrative and exemplary in nature and are not intended to limit the embodiments of the subject matter or the uses of such embodiments. As used in this application, the terms "exemplary" and "illustrative" mean "serving as an example, instance, or illustration." Any implementation described as exemplary or illustrative is not meant to be construed as preferred or advantageous over other implementations. Further, there is no intention to be bound by any expressed or implied theory presented in the preceding background of the invention, the brief summary, or the following detailed description.

The embodiments described herein provide systems and methods that can be used to provide an objective measurable metric that benchmarks PD and/or ND, including its occurrence, radial location and angular dimension. Positive dysphotopsia has been reported as a bright arc or ring. As seen in FIG. 1, an IOL 4 has an anterior surface 5, a posterior surface 6, and an edge 7 between the anterior and posterior surface. Rays may enter the eye at a steep angle. Some rays 1 will miss the IOL completely, while other rays 3 will go through both the anterior and posterior surface. However, some rays 2 will go through the anterior surface and then reflect off of the edge of the IOL. These rays 2 cause the phenomenon associated with positive dysphotopsia.

Negative dysphotopsia has been reported as a dark line or shadow. As seen in FIG. 2, some rays 1 will miss the IOL completely. Other rays 2 will enter through the anterior surface of the IOL. Then they will either refract off of the edge of the IOL as seen by rays 3 or of the posterior side of the IOL as seen by rays 8. Areas 9 and 10 demonstrate areas where no rays are present which lead to the phenomenon associated with negative dysphotopsia. Similarly, area 9 of FIG. 3 is devoid of rays, thus resulting in negative dysphotopsia. FIG. 4 further illustrates negative dysphotopsia and is a top plan view of a cross section of the periphery of the retina with the arc 11 representing the rays 1 that miss the IOL as seen in FIG. 3, and the bright spot 12 representing rays 8 that refract off the posterior side of the IOL as seen in FIG. 3. The area 13 corresponds to area 9 in FIG. 3 and illustrates ND. For reference the fovea 14 is shown in the middle of FIG. 4.

Figure 5:
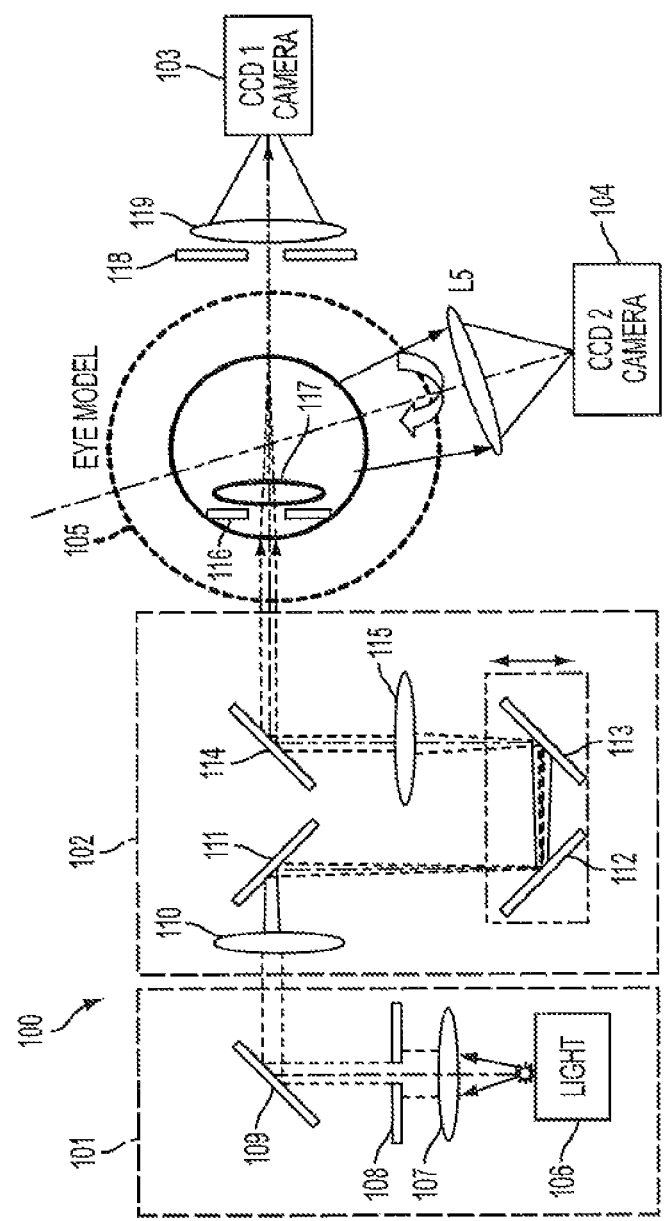
FIG. 5 is a schematic diagram of a system in accordance with an embodiment of the invention.

Turning now to FIG. 5, a schematic diagram of a system for measuring dysphotopsia 100 is illustrated. The system 100 includes a light source 101 configured to provide light energy and a refractor 102 for refracting the light energy into a model eye 105, resulting in some portion of the light passing through the model eye and being received by the first electronic light sensor 103 and the second electronic light sensor 104.

The light source 101 includes a light 106 which produces light energy which may pass through a focusing lens 107 and an aperture 108 before reflecting off of a beam splitter or mirror 109. The aperture 108 may have a filter for selecting the wavelength and/or light intensity. The light intensity may be varied spatially and/or angularly. In general, the light can comprise any suitable source of electromagnetic radiation. Usually a source in or near the visible band of the electromagnetic spectrum will be used. The light source can be configured to generate light in the infrared, near infrared, or ultraviolet bands of the electromagnetic radiation. Furthermore, as used herein, the term "light" may be extended to mean electromagnetic radiation in or near the visible band of the electromagnetic spectrum, for example, in the infrared, near infrared, or ultraviolet bands of the electromagnetic radiation, or to mean electromagnetic radiation detectible by detectors (e.g. CCD) or that is otherwise useful in measuring dysphotopsia. Additionally, the light source can comprise single or multiple distinct sources of light. Furthermore the light source can be monochromatic, polychromatic, polarized, or color-filtered. In some embodiments the light source can be implemented to provide modulated intensity, with the modulated intensity providing the ability to mimic different light conditions. These mimicked conditions can include aberrations, light intensity variations or apodization, and spatial intensity variations.

The light energy then passes from the light source 101 onto the refractor 102 of the system. The refractor may comprise a focusing lens 110, 115 and a series of mirrors 111, 112, 113, 114. In a preferred embodiment the light passes through focusing lens 110 before reflecting off of a series of three mirrors 111, 112, 113. The light then passes through another focusing lens 115 and another mirror 114. Mirrors 112 and 113 may be moveable in order to adjust the focal length.

The light energy then travels through an eye model, e.g. the Average Cornea Eye Model ("ACE") which includes an iris 116 and an intraocular lens 117. Light then passes through the model before being restricted by an aperture 118 and then passing through another focusing lens 119. The aperture 118 and lens 119 are on the optical axis with the iris 116 and intraocular lens 117. The light energy is then received by a first electronic light sensor 103. A second electronic light sensor 104 is coupled to a rotatable guide so that measurements can be taken at any point around the model eye. In lieu of a rotatable guide, an integrating sphere with multiple electronic light sensors, preferably at least 9, may be used.

Figure 7:
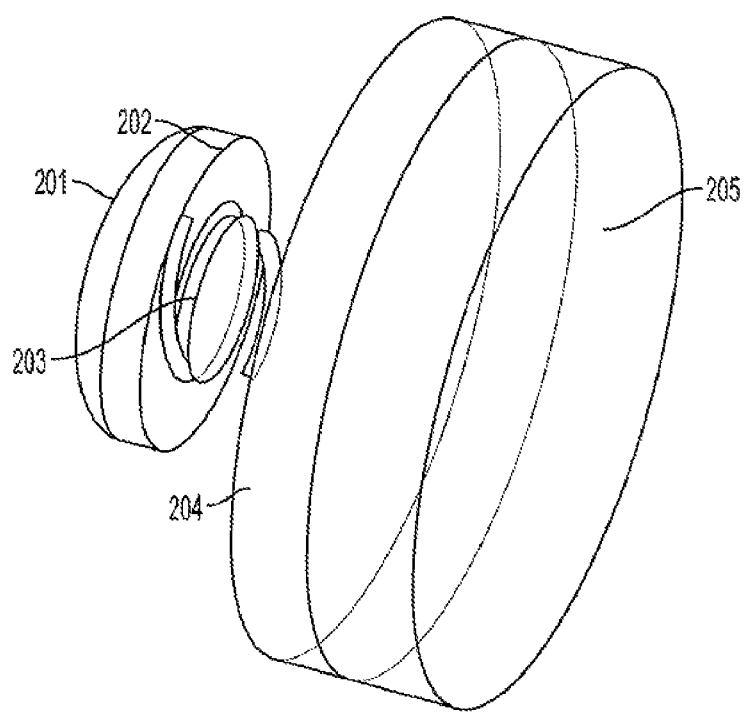
FIG. 7 is the ray-tracing depiction of the measurement set-up used in one of the embodiments of the invention

Alternately, a set-up comprising a physical wide angle eye model can be constructed as depicted in FIG. 7. It comprises a cornea 201, a pupil 202, an IOL holder with the IOL 203, a back window 204 and a flat CCD camera 205. The physical eye model is a ray-tracing based design to enable in-vitro visualization and quantification of various photic events (PD and ND). For a given object angle, pupil size and IOL design and position, the image heights associated with both main and spurious secondary images are theoretically calculated through non-sequential ray-tracing. In order to realistically model the photic effects, a 3D CAD model of the IOL is used to account for its complete geometrical description. Defocusing wise, the native IOL field of curvature or a field of curvature giving an angular aberration profile identical to the one corresponding to the IOL placed in an individualized anatomical eye model with a unique or population averaged retinal shape (conicoid) could be used.

The electronic light sensors can comprise charged-coupled devices (CCD), including both imaging CCDs and intensity CCDs. In other embodiments complementary metal-oxide-semiconductor (CMOS) detectors can be used. In yet other embodiments a wavefront sensor such as a Shack-Hartmann wavefront sensor could be used. Finally, in some embodiments interferometers, photomultiplier tube (PMT) sensors, or small and large angle microscope sensors can be used.

Figure 6:
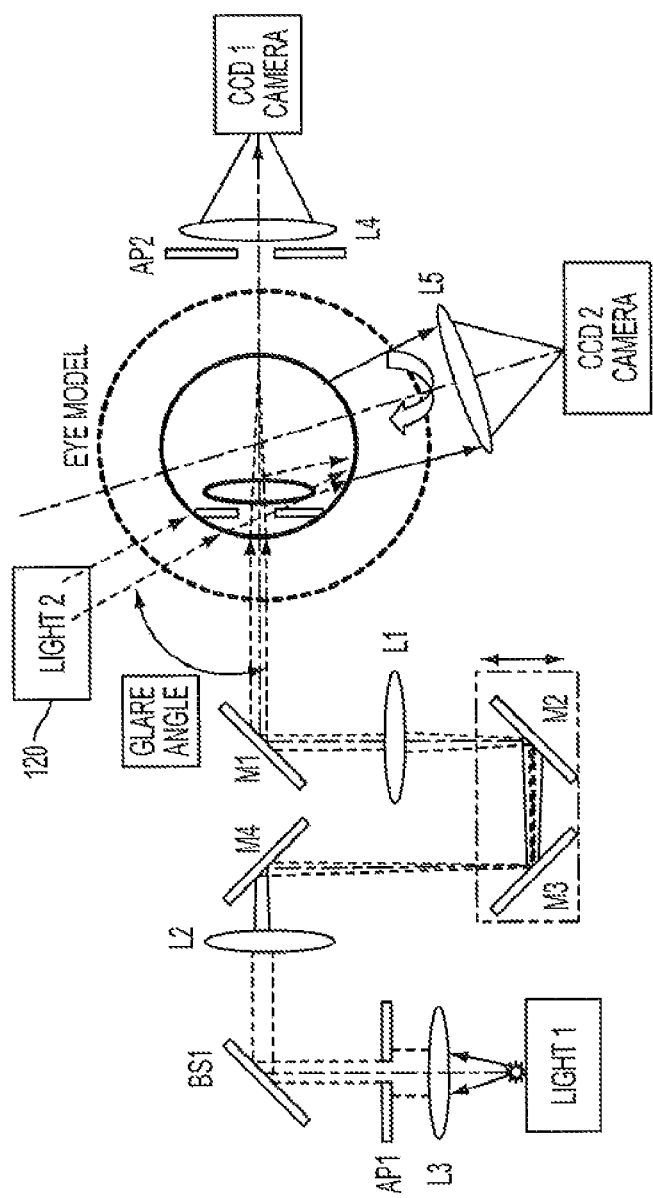
FIG. 6 is a schematic diagram of a system in accordance with an embodiment of the invention.

As seen in FIG. 6, a second light source 120 may be introduced at an angle from the first light source. The angle may be from zero to 110 degrees which covers the typical field of view. The remaining components in FIG. 6 are the same as the components in FIG. 5. Measurement from the system in FIG. 5 can then be compared to measurements from the system in FIG. 6 to determine PD and/or ND. For example, a method for measuring dysphotopsia may comprise illuminating a model eye with a first light source; measuring the light energy introduced by the first light source with a first electronic light sensor stationed behind the model eye and generating first data; measuring the light energy introduced by the first light source with a second electronic light sensor and generating second data, wherein the second light sensor measures the light energy from multiple points around the model eye; illuminating the model eye with a second light source, wherein the second light source introduces light at an angle from the first light source; measuring the light energy introduced by the second light source with the first electronic light sensor and the second electronic light sensor to generate third and fourth data respectively; and analyzing the first data, second data, third data, and fourth data to determine a measurement for dysphotopsia. The light energy introduced by the first and second light source may be measured along the radial direction by the second electronic light sensor. The light energy introduced by the first and second light source may also be measured along the angular direction by the second electronic light sensor.

Using the aforementioned systems, integrated energy (IE) is used as the objective metric to describe the potential occurrence of either positive or negative dysphotopsia of an IOL. The IE is composed of a radial and an angular component. The radial component is the angular integration of energy (AIE) describing the intensity or luminance distribution across the angular meridians while the angular component is the radial integration of energy (RIE) describing the IE across the radius. The former can represent the radial location of the dysphotopsia while the latter can represent the angular dimension of the dysphotopsia. Both the ATE and RIE can be objectively measured or theoretically calculated and can be used to indicate PD or ND. The RI can be further used to indicate the angular range of the dysphotopsia and the AI can be further used to indicate the radial size of the dysphotopsia.

Healthy phakic eyes typically have a non-compromised visual field of about 60 degrees in the nasal, 105 degrees in the temporal, 65 degrees in the superior, and 70 degrees in the inferior orientations. With current circular IOL designs, pseudophakic eyes have a reduced field range with the compromised clinical symptoms described above.

Integration energy (IE) of the light energy or intensity or luminance, $I(r, theta)$ can be measured or calculated along the radial direction (RIB) or the angular direction (AIR) as follows:

$$IE(r) = AIE = A * \text{Integration of } I(r, theta) \text{ over angle from theta1 to theta2 (preferably zero to 360 degrees);} \quad 1)$$

$$IE(theta) = RIE = B * \text{Integration of } I(r, theta) \text{ over radius from center to the edge of lens or the entire light incident angle range;} \quad 2)$$

where A and B are calibration factors (based on initial measurements taken using a calibration lens).

Figure 8:
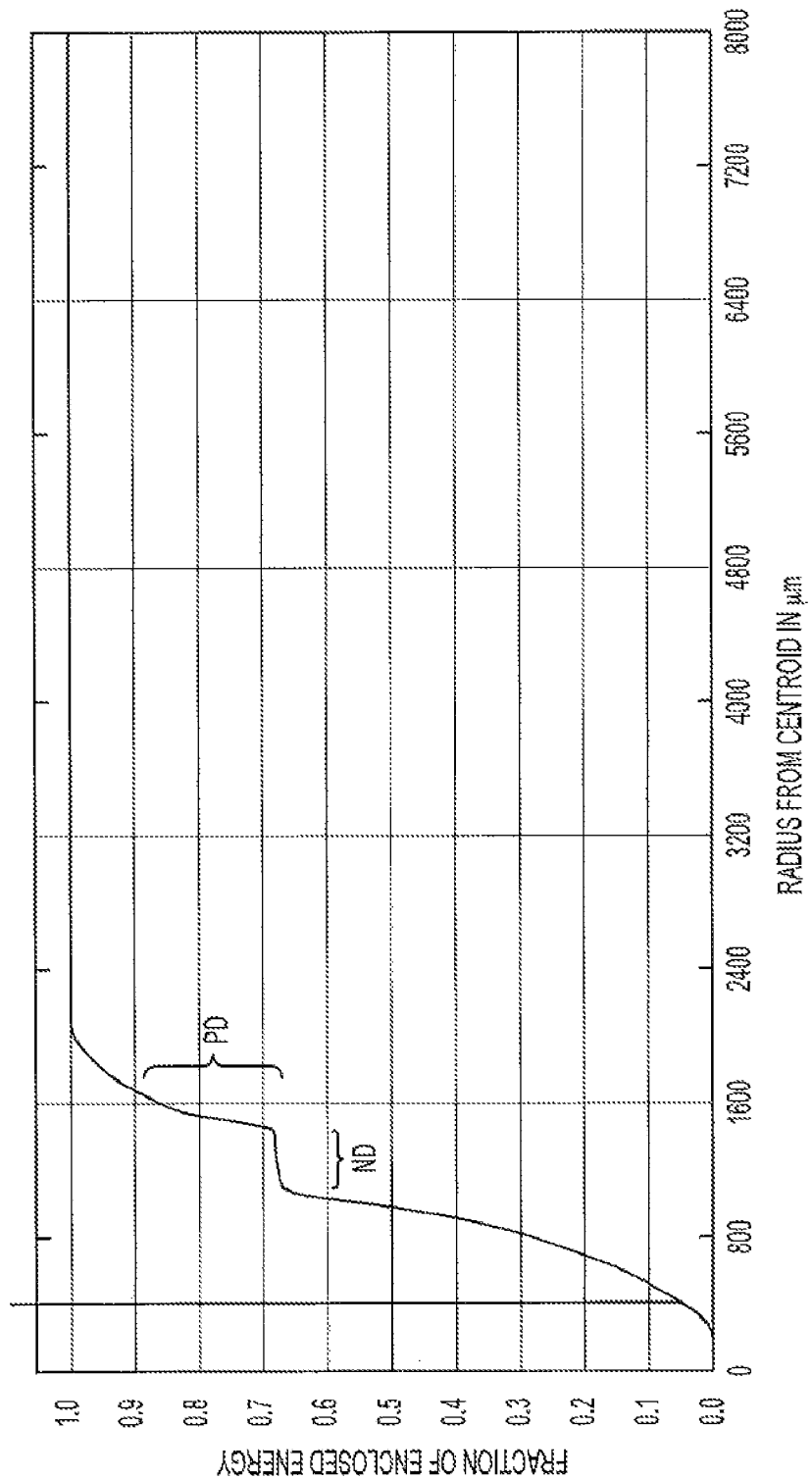
FIG. 8 is a graph illustrating positive and negative dysphotopsia.

By changing the iris radial dimension from zero to a maximum, the ATE may be objectively measured and plotted as shown in the FIG. 8. In a phakic eye with no dysphotopsia, the AIE would be smooth and continuous as r increases from the center to the periphery. However, as seen in FIG. 7, when dysphotopsia exists, there would be an interruption of the IE (r) or ATE curve by a sudden increase range from a PD or there would be an interruption of the IE (theta) or RIE curve by having a flat range from the ND. This middle flat range denoting ND is clearly seen and quantitatively measurable. Similarly, a RIE curve can be objectively measured by changing the iris to a triangle slit and changing the angular dimension from theta 1 such as zero degrees to theta 2 such as 360 degrees.

Figure 9:
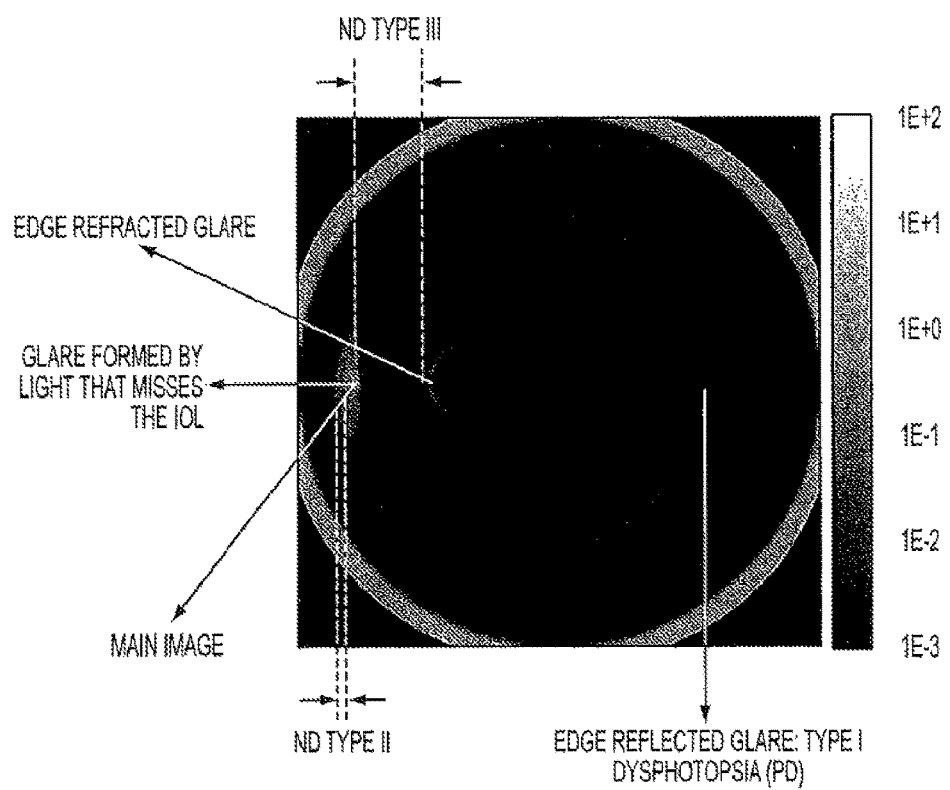
FIG. 9 is a graph illustrating the simulated intensity map at the retina level in a physiological eye model (curved image plane).
Figure 10A:
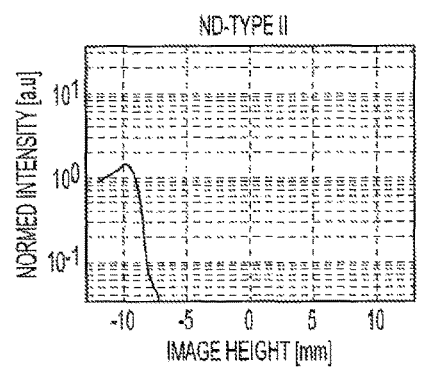
FIGS. 10a-10d are graphs illustrating the measured intensity profiles associated with ND, main image and PD.
Figure 10B:
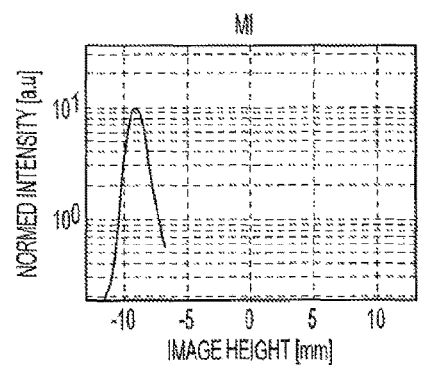
Figure 10C:
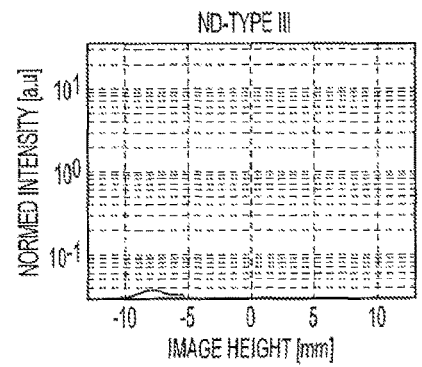
Figure 10D:
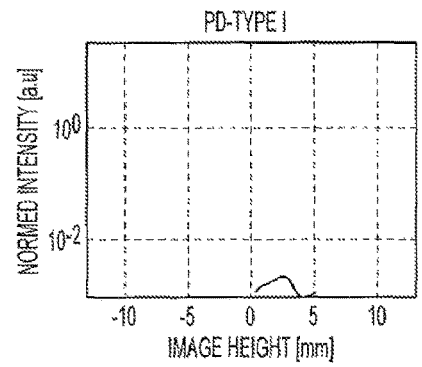

Alternately, as depicted in FIG. 9 which illustrates intensity mapping on the retina level (curved image plane, log scale): ray-tracing result in a physiological eye-model for a given object angle. The dysphotopsia nomenclature uses the one defined in Holladay J T et al, Negative dysphotopsia: the enigmatic penumbra, J Cataract Refract Surg, 2012, 38(7), 1251-65. All photic events can be theoretically assessed for a given object angle, wavelength, eye model configuration and IOL design by mapping the intensity (log scale) on the image plane. The arc shaped positive dysphotopsia (whose geometry is determined by the edge geometry and its spread by the angular magnification) as well as the shadows associated with negative dysphotopsia are well captured. For a given configuration, the glares position (image heights) with respect to the principal image can be used as input information for the in-vitro measurements.

During measurements, for a given object angle, the electronic light sensor is positioned at locations defined by the image heights previously determined (ray-tracing). The measurements output is represented by image frames whose shutter time, defocus and image height is recorded in parallel. The recorded images are analysed off-line by the means of an image processing algorithm and quantified in terms of average per frame intensity, area under the curve, pick intensity image plane position. In order to comparatively assess the light intensity at the principal image and glares positions, each average intensity profile is normalized by the equivalent shutter time (see FIGS. 10a-10d which illustrate photic events for a given object angle described by normed intensity profiles (log 10 scale) as a function of image height: measurement results using a physical eye model (flat image plane) enabling the qualitative and quantitative assessment of ND and PD with respect to the main image (MI)).

This disclosure has been provided in an exemplary form with a certain degree of particularity, and describes the best mode contemplated of carrying out the invention to enable a person skilled in the art to make or use embodiments of the invention. Those skilled in the art will understand, however, that various modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. A system for measuring dysphotopsia, the system comprising:
    a first light source configured to provide light energy to illuminate a model eye;
    a refractor configured to refract the light energy from the first light source and directing the light energy into the model eye;
    a first electronic light sensor configured to measure an amount of light energy in the model eye, wherein the first electronic light sensor is located behind the model eye;
    a second light source configured to provide light energy to illuminate the model eye, wherein the light energy from the second light source is introduced at an angle from the first light source;
    and a second electronic light sensor configured to measure the amount of light energy in the model eye, wherein the second electronic light sensor is capable of taking measurements from various points around the model eye.

2. The system of claim 1, further comprising a focusing lens, an aperture and a beam splitter, wherein the light energy provided by the first light source travels through the focusing lens, aperture, and beam splitter prior to travelling through the refractor.

3. The system of claim 2, wherein the aperture further comprises a filter for varying the wavelength and/or light intensity.

4. The system of claim 1, wherein the refractor is comprised of a plurality of focusing lenses.

5. The system of claim 1, wherein the refractor is comprised of a plurality of mirrors.

6. The system of claim 1, wherein the model eye is the ACE model eye or an eye model that does not have a cornea.

7. The system of claim 1, wherein the model eye has a pupil that is an aperture or a slit.

8. The system of claim 1, wherein the first and second electronic light sensors are selected from the group consisting of: CCD cameras, CMOS detectors, wavefront sensors, and interferometers.

9. The system of claim 1 further comprising a guide upon along which the second electronic light sensor travels in order to take measurements from various points around the model eye.

10. A system for measuring dysphotopsia, the system comprising:
    a first light source configured to provide light energy to illuminate a model eye;
    a refractor configured to refract the light energy from the first light source and directing the light energy into the model eye;
    a first electronic light sensor configured to measure an amount of light energy in the model eye, wherein the first electronic light sensor is located behind the model eye;
    a second light source configured to provide light energy to illuminate the model eye, wherein the light energy from the second light source is introduced at an angle from the first light source;
    and a plurality of electronic light sensors configured to measure the amount of light energy in the model eye at various points around the model eye.

11. The system of claim 10, further comprising a focusing lens, an aperture and a beam splitter, wherein the light energy provided by the first light source travels through the focusing lens, aperture, and beam splitter prior to travelling through the refractor.

12. The system of claim 11, wherein the aperture further comprises a filter for varying the wavelength and/or light intensity.

13. The system of claim 11, wherein the refractor is comprised of a plurality of focusing lenses.

14. The system of claim 11, wherein the refractor is comprised of a plurality of mirrors.

15. The system of claim 11, wherein the model eye is the ACE model eye or an eye model that does not have a cornea.

16. The system of claim 11, wherein the model eye has a pupil that is an aperture or a slit.

17. The system of claim 11, wherein the electronic light sensors are selected from the group consisting of: CCD cameras, CMOS detectors, wavefront sensors, and interferometers.

18. The system of claim 11, wherein the plurality of electronic light sensors are part of an integrating sphere.

* * * * *